United States Patent [19]

George et al.

[11] Patent Number: 5,330,985
[45] Date of Patent: Jul. 19, 1994

[54] 2-AMINO-N-[[4-(AMINOCARBONYL)-PYRIMIDIN-2-YL]AMINO]-ALKYL]PYRIMIDINE-4-CARBOXAMIDE DERIVATIVES, THEIR PREPARATION AND PHARMACEUTICAL COMPOSITIONS CONTAINING THEM

[75] Inventors: Pascal George, St Arnoult en Yvelines; Benoit Marabout, Massy; Jacques Froissant, Brevainville Morée; Jean Pierre Merly, Sceaux, all of France

[73] Assignee: Synthelabo, Le Plessis Robinson, France

[21] Appl. No.: 84,493

[22] Filed: Jul. 1, 1993

[30] Foreign Application Priority Data

Jul. 3, 1992 [FR] France ................ 92 08199
Dec. 14, 1992 [FR] France ................ 92 15037

[51] Int. Cl.$^5$ .................. A61K 31/495; A61K 31/50; C07D 403/02; C07D 403/06
[52] U.S. Cl. ............................. 514/252; 514/275; 544/296
[58] Field of Search ............... 544/296; 514/275, 252

[56] References Cited

U.S. PATENT DOCUMENTS

| | | | |
|---|---|---|---|
| 4,853,387 | 8/1989 | Manoury et al. | 514/252 |
| 5,075,308 | 12/1991 | Ishikawa et al. | 514/252 |
| 5,164,397 | 11/1992 | George et al. | 514/275 |
| 5,210,086 | 5/1993 | George et al. | 514/275 |
| 5,229,392 | 7/1993 | George et al. | 514/275 |

FOREIGN PATENT DOCUMENTS

| | | |
|---|---|---|
| 0416841 | 3/1991 | European Pat. Off. |
| 0435749 | 7/1991 | European Pat. Off. |
| 0480794 | 4/1992 | European Pat. Off. |

OTHER PUBLICATIONS

Chemical Abstracts, vol. 111, No. 3, Jul. 17, 1989, abstract No. 17522e.
Patent Abstracts of Japan, vol. 15, No. 123 (C-816)(4651), Mar. 26, 1991.
Patent Abstracts of Japan, vol. 11, No. 246 (C-439(2693), Aug. 11, 1987.

*Primary Examiner*—Mukund J. Shah
*Assistant Examiner*—Matthew V. Grumbling
*Attorney, Agent, or Firm*—Jacobson, Price, Holman & Stern

[57] ABSTRACT

A compound which is a pyrimidine-4-carboxamide derivative of the general formula (I)

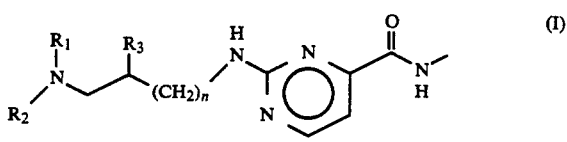

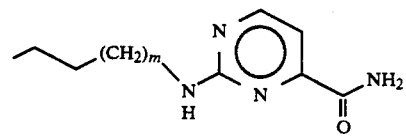

in which
n is 0 or 1, m is 0 or 1,
$R_1$ represents a methyl group when
$R_2$ represents a phenoxy($C_1$-$C_4$)alkyl group (in which the phenoxy group optionally carries 1 or 2 substituents selected from halogen atoms and methoxy groups), or
$R_1$ and $R_2$ form together with the nitrogen atom to which they are attached a 4-phenoxypiperidin-1-yl group (in which the phenoxy group optionally carries 1 or 2 substituents selected from halogen atoms and methoxy groups), a phenoxymethyl-piperidin-1-yl group (in which the phenoxy group optionally carries 1 or 2 $C_1$-$C_4$ alkyl groups) or a 4-phenylpiperazin-1-yl group (in which the phenyl group optionally carries 1 or 2 substituents selected from halogen atoms and methoxy groups), and $R_3$ represents a hydrogen atom or only when n is 1 a hydroxyl group or a methoxy group, or is an addition salt thereof with an acid, is useful as an α-adrenergic antagonist.

7 Claims, No Drawings

2-AMINO-N-[[4-(AMINOCARBONYL)PYRIMIDIN-2-YL]AMINO]-ALKYL]PYRIMIDINE-4-CARBOXAMIDE DERIVATIVES, THEIR PREPARATION AND PHARMACEUTICAL COMPOSITIONS CONTAINING THEM

The present invention relates to 2-amino-N-[[[4-(aminocarbonyl)pyrimidin-2-yl]amino]-alkyl]pyrimidine-4-carboxamide derivatives, their preparation and pharmaceutical compositions containing them.

According to the invention there is provided a compound which is a pyrimidine-4-carboxamide derivative of the general formula (I)

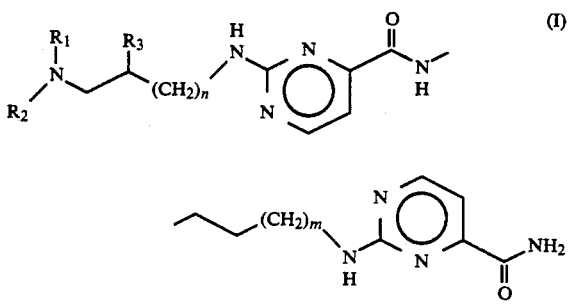

in which
n is 0 or 1, m is 0 or 1, $R_1$ represents a methyl group when
$R_2$ represents a phenoxy($C_1$-$C_4$)alkyl group (in which the phenoxy group optionally carries 1 or 2 substituents selected from halogen atoms and methoxy groups), or $R_1$ and $R_2$ form together with the nitrogen atom to which they are attached a 4-phenoxypiperidin-1-yl group (in which the phenoxy group optionally carries 1 or 2 substituents selected from halogen atoms and methoxy groups), a phenoxymethylpiperidin-1-yl group (in which the phenoxy group optionally carries 1 or 2 $C_1$-$C_4$ alkyl groups) or a 4-phenylpiperazin-1-yl group (in which the phenyl group optionally carries 1 or 2 substituents selected from halogen atoms and methoxy groups), and $R_3$ represents a hydrogen atom or only when n is 1 a hydroxyl group or a methoxy group, or is an addition salt thereof with an acid.

The compounds of the invention may thus exist in the form of bases or of addition salts with acids. Moreover, when the molecule contains an asymmetric carbon atom, a compound may exist in an optically pure form or in the form of a mixture of optical isomers.

In a preferred embodiment $R_1$ and $R_3$ form together with the nitrogen atom to which they are attached a 4-phenylpiperazin-1-yl group in which the phenyl group carries 1 or 2 substituents selected from halogen atoms and methoxy groups, especially a 4-(5-chloro-2-methoxyphenyl)piperazin-1-yl group.

In accordance with the invention, it is possible to prepare the compounds of the invention by a process illustrated in the following scheme.

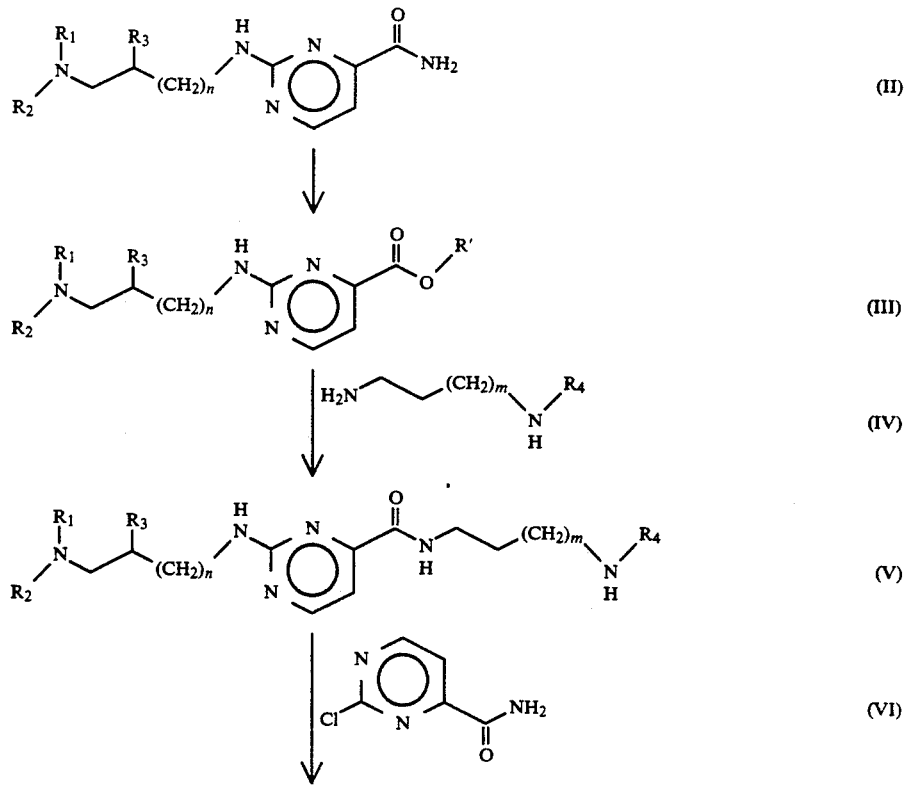

Scheme

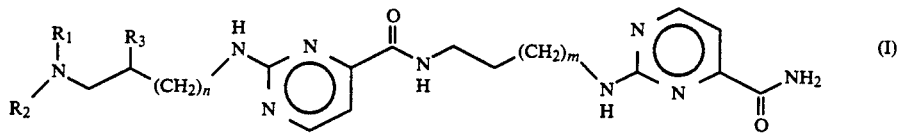

-continued (I)

An amide of general formula (II) (in which $R_1$, $R_2$ and $R_3$ are as defined above) is converted to an ester of general formula (III) (in which R' represents a $C_1$-$C_4$ alkyl group) by reaction with a $C_1$-$C_4$ aliphatic alcohol, for example methanol, in the presence of an acid, for example gaseous hydrochloric acid, at a temperature from 0 to 100° C.

The ester thus obtained is then converted, by reaction with an amine of general formula (IV) (in which $R_4$ represents either a hydrogen atom or an amine protective group, for example a tert-butyloxycarbonyl group), to an amide of general formula (V) in an aliphatic alcohol as solvent, for example methanol, at a temperature from 0° to 60° C.

If necessary, the amine of general formula (V) is then deprotected by a known method, for example by treatment with trifluoroacetic acid in dichloromethane when $R_4$ represents a tert-butyloxycarbonyl group.

Finally, the amine of general formula (V) (in which $R_4$ represents a hydrogen atom) is reacted with 2-chloropyrimidine-4-carboxamide of formula (VI) in an aprotic solvent, for example N,N-dimethylformamide, in the presence of a base, for example potassium carbonate, at a temperature from 20° to 40° C. to obtain the compound of general formula (I). This may then, if desired, be converted into an acid addition salt in known manner.

The 2-aminopyrimidine-4-carboxamide derivatives of general formula (II) may be obtained by methods analogous to those described in FR-A-2675799, FR-A-2678271 and EP-A-480794.

The monoprotected diamines of general formula (IV) may be prepared by methods analogous to those described in Synthesis (1984) 1032–1033 and Synthesis (1990) 366–368.

The following Examples illustrate in detail the preparation of a number of compounds according to the invention. The structures of the compounds obtained were confirmed by elemental microanalyses and IR and NMR spectra.

The numbers of the compounds, shown in brackets in the titles, correspond to those in the Table given later.

EXAMPLE 1 (COMPOUND NO. 4 )

N-[2-[[4-(Aminocarbonyl)pyrimidin-2-yl]amino ]ethyl]-2-[[3-[4-(5-chloro-2-methoxyphenyl)piperazin-1 -yl]propyl]amino]pyrimidine-4-carboxamide hydrochloride 1.1. Methyl 2-[[3-[4-(5-chloro-2-methoxyphenyl)-piperazin-1-yl]propyl]amino]pyrimidine-4-carboxylate 7.8 g (19.2 retool) of 2-[[3-[4-(5-chloro-2-methoxyphenyl)piperazin-1-yl]propyl]amino]pyrimidine-4-carboxamide are introduced into 300 ml of methanol in a 0.5 l round-bottomed flask, a stream of gaseous hydrochloric acid is passed through for a few minutes and the mixture is heated at the reflux temperature of the methanol for 1 h 45. The solvent is evaporated under reduced pressure, 200 ml of dichloromethane are added to the residue and the mixture is cooled to 0° C. The mixture is basified with a saturated aqueous sodium hydrogencarbonate solution. The organic phase is dried over sodium sulphate, filtered and the solvent is then evaporated under reduced pressure. The residue is purified by chromatography on a silica gel column (eluent: 100/0 to 90/10 dichloromethane/methanol mixture) and then by recrystallisation from cyclohexane. 5.84 g (13.9 mmol) of ester are isolated.

Melting point: 118.5°–119° C.

1.2. 1,1-Dimethylethyl 2-[[[2-[[3-[4-(5-chloro-2-methoxyphenyl)piperazin-1-yl]propyl]amino]-pyrimidin-4-yl]carbonyl]amino]ethylcarbamate 5.07 g (31.65 mmol) of 1,1-dimethylethyl 2-aminoethylcarbamate and 10 g (23.8 mmol) of methyl 2-[[3-[4-(5 -chloro-2-methoxyphenyl)piperazin-1-yl]propyl]amino]-pyrimidine-4-carboxylate are introduced into 50 ml of 2-propanol in a 500 ml round-bottomed flask and the mixture is heated at reflux for 14 h. The solvent is evaporated under reduced pressure and the residue is purified by chromatography on a silica gel column (100/0 to 90/10 dichloromethane/methanol eluent) to produce 10.77 g (19.65 mmol) of a compound in the form of an oil, which is used as is in the following stage.

1.3. N- (2-Aminoethyl) -2-[[3-[4- (5-chloro-2-methoxyphenyl)piperazin-1-yl ]propyl amino]pyrimidine-4-carboxamide 10.77 g (19.65 retool) of 1,1-dimethylethyl 2-[[[2-[[3-[4-(5-chloro-2-methoxyphenyl) piperazin-1-yl]propyl]amino]pyrimidin-4-yl]carbonyl]amino]ethylcarbamate compound are introduced into 50 ml of water in a 0.5 l round-bottomed flask and then 25 ml of concentrated hydrochloric acid are introduced dropwise. The mixture is cooled to 0° C. with an ice/salt/water mixture and then 30% sodium hydroxide solution is added portionwise until the pH is basic. Extraction is carried out with dichloromethane, the organic phase is dried over sodium sulphate, filtered and the solvents are evaporated under reduced pressure, and 8.8 g (19.65 mmol) are obtained of an oil which is used as is in the following stage.

1.4. N- [2-[[4-(Aminocarbonyl)pyrimidin-2-yl]amino ]-ethyl]-2-[[3-[4-(5-chloro-2-methoxyphenyl)-piperazin-1-yl]propyl]amino]pyrimidine-4-carboxamide hydrochloride 8.8 g (19.65 mmol) of N-(2-aminoethyl)-2-[[3-[4-(5-chloro-2-methoxyphenyl)piperazin-1-yl]propyl]-amino]pyrimidine-4-carboxamide, 3.1 g (19.7 mmol) of 2-chloropyrimidine-4-carboxamide and 4.0 g (29 mmol) of potassium carbonate are introduced, under an argon atmosphere, into 250 ml of acetonitrile in a 0.5 l round-bottomed flask and the mixture is heated at reflux for 18 h.

The mixture is cooled to room temperature, the insoluble material is collected by filtration and then washed with water. The product obtained is dissolved in a dichloromethane/methanol mixture and then purified by chromatography on a silica gel column (100/0 to 85/15 dichloromethane/methanol eluent). After recrystallisation from an acetonitrile/dichloromethane mixture, 7.03 g (12.35 mmol) of compound are obtained in the base form. Melting point: 196°–199° C.

In order to prepare the hydrochloride, 3.03 g (5.32 mmol) of it are dissolved in a mixture of 50 ml of dichloromethane and 50 ml of methanol, and 53.2 ml of a 0.1N solution of hydrochloric acid in 2-propanol are added. The solvents are evaporated under reduced pressure and the residue is recrystallised from a mixture of methanol and ethyl acetate. 2.63 g of hydrochloride are finally obtained.

Melting point: 197.5°–200.5° C.

EXAMPLE 2 (COMPOUND NO. 11)

N-[2-[[4-(Aminocarbonyl)pyrimidin-2-yl]amino]ethyl]-2-[[2-[4-(2,5-dimethoxyphenyl)piperazin-1-yl]ethyl]amino]pyrimidine-4-carboxamide 2.1. Methyl 2-[[2-[4-(2,5-dimethoxyphenyl)piperazin-1-yl]ethyl]amino]pyrimidine-4-carboxylate 8.76 g (22.66 mmol) of 2-[[2-[4-(2,5-dimethoxyphenyl)piperazin-1-yl]ethyl]amino]pyrimidine-4-carboxamide are introduced into 650 ml of methanol in a 1 l round-bottomed flask, a stream of gaseous hydrochloric acid is passed through for a few minutes and the mixture is then heated at the reflux temperature of the methanol for 5 h. The solvent is evaporated under reduced pressure, 300 ml of dichloromethane are added to the residue and the mixture is then basified with a saturated aqueous sodium hydrogencarbonate solution. The organic phase is dried over sodium sulphate, filtered and the solvent is then evaporated under reduced pressure. After purification by chromatography on a silica gel column (eluent: 100/0 to 90/10 dichloromethane/methanol mixture) and then by recrystallisation from cyclohexane, 6.93 g (17.26 mmol) of ester are isolated.

Melting point: 85.5°–87° C.

2.2. N-(2-Aminoethyl) -2-[[2-[4-(2,5-dimethoxyphenyl)piperazin-1-yl]ethyl]amino]pyrimidine-4-carboxamide 1.5 g (3.74 retool) of methyl 2-[[2-[4-(2,5-dimethoxyphenyl)piperazin- 1-yl]ethyl]amino]pyrimidine-4-carboxylate are introduced into 20 ml of dichloromethane and 150 ml of methanol in a 0.25 l round-bottomed flask and then 3 ml of ethylenediamine (2.7 g, 44.9 mmol) are introduced.

The mixture is stirred for 4 h at room temperature and the solvents are then evaporated under reduced pressure.

The crude residue is dissolved in 150 ml of dichloromethane and the organic phase is washed five times with water. The organic phase is dried over sodium sulphate, filtered and the solvent is evaporated under reduced pressure, and 1.6 g (3.74 mmol) are obtained of an oil which is used as is in the following stage.

2.3. N-[2-[[4-Aminocarbonyl)pyrimidin-2-yl]amino]ethyl]-2-[[2-[4-(2,5-dimethoxyphenyl)piperazin-1-yl]ethyl]amino]pyrimidine-4-carboxamide 1.6 g (3.74 mmol) of N-(2-aminoethyl)-2-[[2-[4-(2,5-dimethoxyphenyl) piperazin-1-yl]ethyl]amino]pyrimidine-4-carboxamide, 0.59 g (3.74 mmol) of 2-chloropyrimidine-4-carboxamide and 0.8 g (5.8 mmol) of potassium carbonate are introduced into 200 ml of acetonitrile in a 0.5 l round-bottomed flask and the mixture is heated at reflux for 16 h.

The solvent is evaporated under reduced pressure and 200 ml of water and 500 ml of dichloromethane are added to the crude residue. The organic phase is dried over sodium sulphate, the solvent is then evaporated under reduced pressure, and the residue is purified by chromatography on a silica gel column (eluent: 100/0 to 90/10 dichloromethane/methanol mixture) and then by recrystallisation from an acetonitrile/dichloromethane mixture. 1.1 g (2 mmol) of compound are obtained.

Melting point: 158°–160° C.

EXAMPLE 3 (COMPOUND NO. 12)

N-[2-[[4-(Aminocarbonyl)pyrimidin-2-yl]amino]ethyl]-2-[[3-[[2-(2-methoxyphenoxy)ethyl]methylamino]propyl]amino]pyrimidine-4-carboxamide 3.1. Methyl 2-[[3-[[2-(2-methoxyphenoxy)ethyl]methylamino]propyl]amino]pyrimidine-4-carboxylate 12.7 g (35.3 mmol) of 2-[[3-[[2-(2-methoxyphenoxy)ethyl]methylamino]propyl]amino]pyrimidine-4-carboxamide and 300 ml of methanol are introduced into a 0.5 l round-bottomed flask, a stream of gaseous hydrochloric acid is passed through for a few minutes and the mixture is heated at the reflux temperature of the methanol for 4 h.

The solvent is evaporated under reduced pressure, 100 ml of dichloromethane are added to the residue and the mixture is cooled to 0° C. The mixture is basified with a saturated aqueous sodium hydrogencarbonate solution, the layers are separated and the organic phase is dried over sodium sulphate, filtered and the solvent is then evaporated under reduced pressure. After purification by chromatography on a silica gel column (eluent: dichloromethane/methanol mixture, 96/4 to 88/12), 8.7 g of compound are isolated in oily form, which compound is used as is in the following stage.

3.2. N- (2-Aminoethyl) -2-[[3-[[2- (2-methoxyphenoxy)ethyl]methylamino]propyl]amino]pyrimidine-4-carboxamide.

3.0 g (8 mmol) of methyl 2-[[3-[[2-(2-methoxyphenoxy)ethyl]methylamino]propyl]amino]pyrimidine-4-carboxylate and 4.8 g (80 mmol) of ethylenediamine are introduced into 100 ml of a 1/1 mixture of methanol/dichloromethane in a 0.25 l, three-necked, round-bottomed flask. The reaction mixture is stirred for 48 h at room temperature and the solvents are then evaporated under reduced pressure.

The crude residue is taken up in 100 ml of dichloromethane, the organic phase is washed with water (2×100 ml), dried over sodium sulphate, filtered and then the solvent is evaporated under reduced pressure to produce 3.05 g of compound in oily form, which compound is used as is in the following stage.

3.3 N-[2-[[4- (Aminocarbonyl)pyrimidin-2-yl]amino]-ethyl]-2-[[3-[[2-(2-methoxyphenoxy)ethyl]methylamino]propyl]amino]pyrimidine-4-carboxamide 3.0 g (7.45 mmol) of N-(2-aminoethyl)-2-[[3-[[2-(2-methoxyphenoxy) ethyl]methylamino]propyl]amino]pyrimidine-4-carboxamide, 1.23 g (7.8 mmol) of 2-chloropyrimidine-4-carboxamide, 1.55 g (11.2 mmol) of potassium carbonate and 0.1 g of sodium iodide are introduced into 40 ml of N,N-dimethylformamide in a 0.25 l, three-necked, round-bottomed flask and the reaction mixture is heated at 60° C. for 15 h. The mixture is cooled to room temperature and the reaction product is poured onto 100 ml of water and extracted with ethyl acetate (3×100 ml). The organic phase is washed with water, dried over sodium sulphate, filtered and the solvents are evaporated under reduced pressure. After recrystallisation from ethyl acetate, 1.95 g of compound are obtained.

Melting point: 131°–133° C.

EXAMPLE 4 (COMPOUND NO. 13)

N-[2-[[4-(Aminocarbonyl)pyrimidin-2-yl]amino]ethyl]-2-[[3-[4-[[5-methyl-2-(1-methylethyl)phenoxy]methyl]-piperidin-1-yl]propyl]amino]pyrimidine-4-carboxamide 4.1. Methyl 2-[[3-[4-[[5-methyl-2-(1-methylethyl)-phenoxy] methyl]piperidin-1-yl]propyl]amino]pyrimidine-4-carboxylate 6.3 g (14.8 mmol) of 2-[[3-[4-[[5-methyl-2-(1-methylethyl)phenoxy]methyl]piperidin-1-yl]propyl]amino]-pyrimidine-4-carboxamide and 250 ml of methanol are introduced into 1 l round-bottomed flask, a stream of gaseous hydrochloric acid is passed through for a few minutes and the mixture is heated at the reflux temperature of the methanol for 1 h 30.

The solvent is evaporated under reduced pressure, 150 ml of dichloromethane are added to the residue and the mixture is cooled to 0° C. The mixture is basified with a saturated aqueous sodium hydrogencarbonate solution, the layers are separated and the organic phase is dried over magnesium sulphate, filtered and the solvent is then evaporated under reduced pressure.

After purification by chromatography on a silica gel column (eluent: dichloromethane/methanol mixture, 100/0 to 90/10), 4.3 g of compound are isolated in oily form, which compound is used as is in the following stage.

4.2.1,1-Dimethylethyl 2-[[[2-[[3-[4-[[5-methyl-2-(1-methylethyl)phenoxy]methyl]piperidin-1-yl]propyl-]amino]pyrimidin-4-yl]carbonyl]amino]ethyl-carbamate 4.3 g (9.76 mmol) of methyl 2-[[3-[4-[[5-methyl-2-(1-methylethyl)phenoxy]methyl]piperdin-1-yl]propyl-]amino]pyrimidine-4-carboxylate and 1.9 g (11.7 mmol) of 1,1-dimethylethyl 2-aminoethylcarbamate are introduced into 15 ml of 2/1 mixture of 2-propanol/methanol in a 0.1 l round-bottomed flask and the mixture is heated at reflux for 10 h.

The solvent is evaporated under reduced pressure and the residue is purified on a neutral alumina column (eluent: cyclohexane/ethyl acetate, 80/20 to 0/100) to produce 2.8 g of compound in the form of an oil, which compound is used as is in the following stage.

4.3. N-(2-Aminoethyl)-2-[[3-[4-[[5-methyl-2-(1-methyl ethyl) phenoxy]methyl]piperidin-1-yl]propyl]amino]-pyrimidine-4-carboxamide 2.8 g (4.92 mmol) of 1,1-dimethylethyl 2-[[[2-[[3-[4-[[5-methyl-2-(1-methylethyl)phenoxy]methyl]piperidin-1-yl]propyl]amino]pyrimidin-4-yl]carbonyl]amino]e-thylcarbamate in solution in 20 ml of dichloromethane are introduced into a 0.25 l round-bottomed flask, 20 ml of trifluoroacetic acid are then added and the mixture is heated at reflux for 5 h.

The solvents are evaporated under reduced pressure, and 70 ml of water and then 1N sodium hydroxide solution are added to the crude residue. Extraction is carried out with dichloromethane (3×150 ml) and then the organic phase is washed with water (100 ml), dried over sodium sulphate, filtered and the solvent is then evaporated under reduced pressure. 2.31 g of compound are obtained in the form of an oil, which compound is used as is in the following stage.

4.4. N-[2-[[4- (Aminocarbonyl) pyrimidin-2-yl]amino]-ethyl]-2-[[3-[4-[[5-methyl-2- (1-methylethyl)phenoxy]-methyl]piperidin-1-yl]propyl]amino]pyrimidine-4-carboxamide 2.31 g (4.92 mmol) of N-(2-aminoethyl)-2-[[3-[4-[[5-methyl-2-(1-methylethyl)phenoxy]methyl]piperidin-1-yl]propyl]amino]pyrimidine-4-carboxamide, 0.82 g (5.2 mmol) of 2-chloropyrimidine-4-carboxamide, 0.89 g (6.4 mmol) of potassium carbonate and 75 ml of acetonitrile are introduced, under an argon atmosphere, into a 0.25 l round-bottomed flask and the mixture is heated at reflux for 30 h.

The solvent is evaporated, 100 ml of water are then added to the crude residue and extraction is carried out with dichloromethane (3×100 ml). The organic phase is washed with water (100 ml), dried over sodium sulphate, filtered and the solvent is then evaporated under reduced pressure. The product is purified by chromatography on a silica gel column (dichloromethane/methanol eluent, 100/0 to 90/10) and recrystallised from acetonitrile. 1.75 g of compound are finally isolated.

Melting point: 164°-167° C.

EXAMPLE 5 (COMPOUND NO. 15).

(±) -N-[2-[[4- (Aminocarbonyl) pyrimidin-2-yl]amino]-ethyl]-2 -[[3-[4-(5-chloro-2-methoxyphenyl)piperazin-1-yl]-2-hydroxypropyl]amino]pyrimidine-4-carboxamide 5.1. Methyl (±)-2-[[3-[4-(5-chloro-2-methoxyphenyl)-piperazin-1-yl]-2-hydroxypropyl]amino]pyrimidine-4-carboxylate.

4.7 g. (11.16 mmol) of (±)-2-[[3-[4-(5-chloro-2-methoxyphenyl) piperazin-1-yl]-2-hydroxypropyl-]amino]pyrimidine-4-carboxamide and 450 ml of methanol are introduced into a 1 l round-bottomed flask, a stream of gaseous hydrochloric acid is passed through for a few minutes and the mixture is heated at the reflux temperature of the methanol for 2 h.

The solvent is evaporated under reduced pressure, 300 ml of dichloromethane are added to the residue and the mixture is cooled to 0° C. The mixture is basified with a saturated aqueous sodium hydrogencarbonate solution, the layers are separated and the aqueous phase is again extracted with dichloromethane. The organic phase is dried over sodium sulphate, filtered and the solvent is evaporated under reduced pressure. The product is purified by chromatography on a silica gel column (eluent: dichloromethane/methanol mixture, 100/0 to 90/10) and recrystallised from cyclohexane. 3.07 g of ester are obtained.

Melting point: 119°-122° C.

5.2.1,1-Dimethylethyl (±)-2-[[[2-[[3-[4-(5-chloro-2 -methoxyphenyl) piperazin-1-yl]-2-hydroxypropyl]amino]-pyrimidin-4-yl]carbonyl]amino]-ethylcarbamate 2.21 g (5.07 mmol) of methyl (±)-2-[[3-[4-(5-chloro-2-methoxyphenyl)piperazin-1-yl]-2-hydroxypropyl-]amino]pyrimidine-4-carboxylate and 2.6 g (16.2 mmol) of 1,1-dimethylethyl 2-aminoethylcarbamate are introduced into 25 ml of 2-propanol in a 0.25 l round-bottomed flask and the reaction mixture is heated for 16 h.

The solvent is evaporated under reduced pressure and the crude product is purified by chromatography on a silica gel column (eluent: dichloromethane/methanol, 100/0 to 90/10). 2.8 g of a pasty compound are obtained, which compound is used as is in the following stage. 5.3. (±)-N-(2-Aminoethyl)-2-[[3-[4-(5-chloro-2-methoxyphenyl)piperazin-1-yl]-2-hydroxypropyl-]amino]pyrimidine-4 -carboxamide 2.8 g (4.96 mmol) of 1,1-dimethylethyl (±)-2-[[[2-[[3-[4-(5-chloro-2-methoxyphenyl)piperazin-1-yl]-2-hydroxypropyl]amino]pyrimidin-4-yl]carbonyl-]amino]ethylcarbamate in solution in a few ml of methanol are introduced into a 0.5 l round-bottomed flask and then 7 ml of concentrated hydrochloric acid are introduced dropwise. After stirring for 15 min, the mixture is cooled to 0° C with an ice/salt/water mixture and then 1N sodium hydroxide solution is added in small portions until the pH is basic. Extraction is carried out with dichloromethane, the organic phase is dried over sodium sulphate, filtered and the solvents are evaporated under reduced pressure. 2.3 g of an oil are obtained, which oil is used as is in the following stage.

5.4. (±)-N-[2-[[4-(Aminocarbonyl)pyrimidin-2-yl]amino]ethyl]-2-[[3-[4-(5-chloro-2-methoxyphenyl)-piperazin-1-yl]-2-hydroxypropyl]amino]pyrimidine-4-carboxamide 2.32 g (4.96 mmol) of (±)-N-(2-aminoethyl)-2-[[3-[4-(5-chloro-2-methoxyphenyl) piperazin-1-yl]-2-hydroxypropyl]amino]pyrimidine-4-carboxamide, 0.8 g (5.1 mmol) of 2-chloropyrimidine-4-carboxamide and 1 g (7.2 mmol) of potassium carbonate are introduced, under an argon atmosphere, into 150 ml of acetonitrile in a 0.5 l round-bottomed flask and the mixture is heated at reflux for 17 h.

The mixture is cooled to room temperature, the insoluble material is collected by filtration and purified by chromatography on a silica gel column (eluent: 100/0 to 85/15 dichloromethane/methanol). 0.6 g of compound is isolated after recrystallisation from acetonitrile.

Melting point: 178°–181° C.

The following table illustrates the chemical structures and the physical properties of a number of compounds according to the invention.

TABLE (I)

| No. | —NR₁R₂ | R₃ | n | m | Salt | M.p. (°C.) |
|---|---|---|---|---|---|---|
| 1 | Cl-phenyl-piperazin-N— | H | 1 | 0 | —<br>fum⁽¹⁾ | 158–161<br>173–177 |
| 2 | Cl-phenyl-piperazin-N— | H | 0 | 0 | —<br>HCl.H₂O | 195.5–198<br>167–171 |
| 3 | Cl-(OCH₃)-phenyl-piperazin-N— | H | 1 | 1 | — | 119–121 |
| 4 | Cl-(OCH₃)-phenyl-piperazin-N— | H | 1 | 0 | HCl<br>fum | 197.5–200.5<br>175–178 |
| 5 | Cl-(OCH₃)-phenyl-piperazin-N— | H | 0 | 1 | — | 146–147 |
| 6 | Cl-(OCH₃)-phenyl-piperazin-N— | H | 0 | 0 | — | 189–191 |

TABLE-continued
(I)
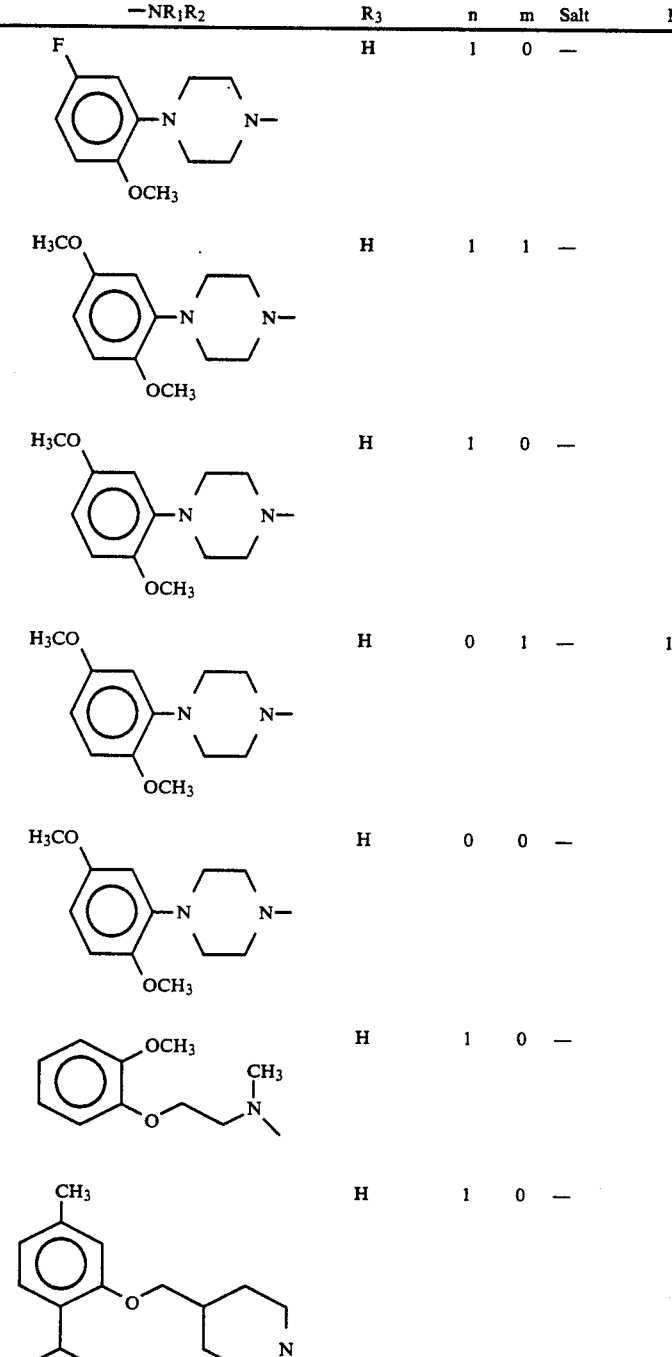
| No. | —NR₁R₂ | R₃ | n | m | Salt | M.p. (°C.) |
|---|---|---|---|---|---|---|
| 7 | 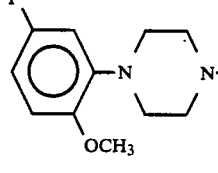 | H | 1 | 0 | — | 180–182 |
| 8 | 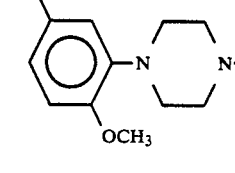 | H | 1 | 1 | — | 110–112 |
| 9 | 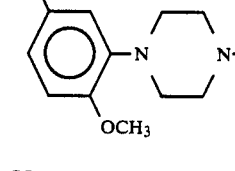 | H | 1 | 0 | — | 181–184 |
| 10 | 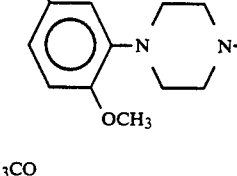 | H | 0 | 1 | — | 115.5–117.5 |
| 11 | 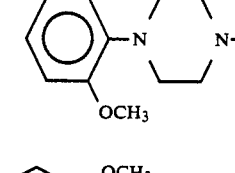 | H | 0 | 0 | — | 158–160 |
| 12 | 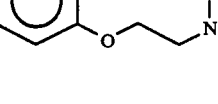 | H | 1 | 0 | — | 131–133 |
| 13 | 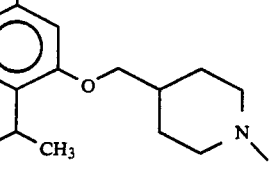 | H | 1 | 0 | — | 164–167 |
| 14 | 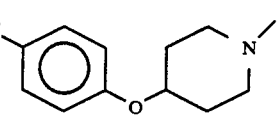 | H | 1 | 0 | — | 167–168 |

TABLE-continued

![Formula I structure]

| No. | —NR₁R₂ | R₃ | n | m | Salt | M.p. (°C.) |
|---|---|---|---|---|---|---|
| 15 | Cl-C₆H₃(OCH₃)-N(piperazine)N— | OH | 1 | 0 | —[2] | 178–181 |
| 16 | Cl-C₆H₃(OCH₃)-N(piperazine)N— | OCH₃ | 1 | 0 | —[2] | 143.5–145 |

Notes: in the "Salt" column, "—" denotes a compound in the base form, "fum" denotes a fumarate, "HCl" denotes a hydrochloride and "H₂O" denotes a monohydrate salt;
[1]Compound No. 1 contains 0.25 mol of acid per 1 mol of base;
[2]Compounds No. 15 and 16 are racemates.

The compounds of the invention were subjected to studies of their antagonist activity with respect to $\alpha_1$-adrenergic receptors in the lower urinary tract.

Their in vitro activity was studied on isolated rabbit urethra.

Rings of adult male rabbit urethra are prepared according to the method of Ueda et al., Eur. J. Pharmacol., (1984), 103, 249–254, and then, after sensitisation to noradrenaline, the curve of concentration-response to phenylephrine is determined in the absence and presence of the test compound.

The potency of the $\alpha_1$-adrenergic antagonism of each compound is evaluated by calculating the $pA_2$, the antilogarithm of the molar concentration of antagonist in the presence of which the agonist concentration must be doubled in order to generate the same effect as in its absence.

The $pA_2$ values of the compounds are of the order of 7 to 10.

The in vivo activity of the compounds of the invention was studied in respect of their effect on urethral hypertonia generated by stimulation of the sympathetic fibres of the hypogastric nerve in anaesthetized cats.

Adult male cats are anaesthetized with pentobarbitone sodium, and prepared according to the method of Theobald, J. Auton. Pharmac., (1983), 3, 235–239, so as to obtain a urethral hypertonia by stimulation of the sympathetic fibres of the hypogastric nerve. The contractile responses of the urethra to electrical stimulation of the hypogastric nerve are noted before and after intravenous administration of the test compounds at cumulative doses from 1 to 1,000 μg/kg.

The potency of the $\alpha_1$-adrenergic antagonism of each compound is evaluated by calculating the $ID_{50}$, the dose which inhibits urethral hypertonia by 50%.

The $ID_{50}$ values of the compounds of the invention are of the order of 0.01 to 1 mg/kg.

The results of the tests show that the compounds of the invention show in vitro an antagonist activity with respect to the $\alpha_1$-adrenergic receptors of the smooth muscles of the lower urinary tract (urethra) when the muscles are stimulated by an $\alpha_1$-adrenergic agonist (phenylephrine). In vivo, they inhibit urethral hypertonia generated by stimulation of the sympathetic nervous system.

The compounds of the invention can hence be used for the symptomatic treatment of diseases and conditions involving a hyperactivity of the $\alpha$-adrenergic system in the lower urinary tract, and in particular for the treatment of urinary disorders of benign hypertrophy of the prostate, such as dysuria and pollakiuria.

For this purpose, they may be presented in all forms suited to enteral or parenteral administration, in combination with pharmaceutical excipients, for example in the form of tablets, dragees, capsules including hard gelatin capsules, solutions or suspensions to be taken by mouth or injected, and suppositories, their content being such as to permit a daily dose of 0.1 to 500 mg of active substance.

We claim:

1. A compound which is a pyrimidine-4-carboxamide derivative of the formula (I)

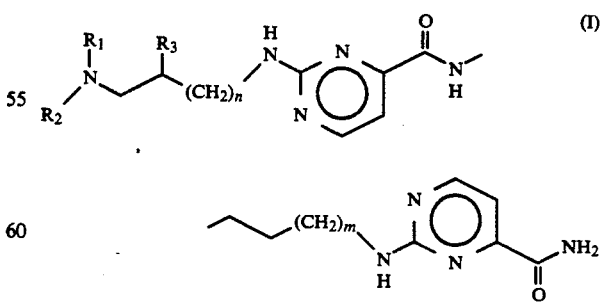

in which
n is 0 or 1, m is 0 or 1,
R₁ represents a methyl group when
R₂ represents a phenoxy(C₁–C₄)alkyl group (in which the phenoxy group optionally carries 1 or 2 substituents selected from halogen atoms and methoxy groups), or $R_1$ and $R_3$ form together with the nitrogen atom to which they are attached a 4-phenoxypiperidin-1-yl group (in which the phenoxy group optionally carries 1 or 2 substituents selected from halogen atoms and methoxy groups), a phenoxymethylpiperidin-1-yl group (in which the phenoxy group optionally carries 1 or 2 $C_1$–$C_4$ alkyl groups) or a 4-phenylpiperazin-1-yl group (in which the phenyl group optionally carries 1 or 2 substituents selected from halogen atoms and methoxy groups), and $R_3$ represents a hydrogen atom or only when n is 1 a hydroxyl group or a methoxy group, or is an addition salt thereof with an acid.

2. A compound according to claim 1, wherein $R_1$ and $R_2$ form together with the nitrogen atom to which they are attached a 4-phenylpiperazin-1-yl group in which the phenyl group carries 1 or 2 substituents selected from halogen atoms and methoxy groups.

3. A compound according to claim 1, wherein $R_1$ and $R_2$ form together with the nitrogen atom to which they are attached a 4-(5-chloro-2-methoxy-phenyl)piperazin-1-yl group.

4. A compound according to claim 1, wherein any halogen substituent on a phenoxy or phenyl group is chloro or fluoro.

5. N-[2-[[4-(Aminocarbonyl)pyrimidin-2-yl]amino]ethyl]-2-[[3-[4-(5-chloro-2-methoxyphenyl)piperazin-1-yl]propyl]amino]pyrimidine-4-carboxamide or an acid addition salt thereof.

6. A method for the symptomatic treatment of diseases and conditions involving hyperactivity of the α-adrenergic system in the lower urinary tract, which comprises administering to a patient suffering from such a disease or condition an effective amount of, as α-adrenergic inhibitor, a compound as claimed in claim 1.

7. A pharmaceutical composition which contains a compound as claimed in claim 1 in association with a pharmaceutical excipient.

* * * * *